(12) United States Patent
Hajishah et al.

(10) Patent No.: US 9,775,742 B2
(45) Date of Patent: Oct. 3, 2017

(54) VITRECTOMY SURGICAL APPARATUS EMPLOYING MULTISENSOR PRESSURE FEEDBACK

(71) Applicant: ABBOTT MEDICAL OPTICS INC., Santa Ana, CA (US)

(72) Inventors: Abraham Hajishah, Irvine, CA (US); Mitchell W Mallough, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 93 days.

(21) Appl. No.: 14/692,974

(22) Filed: Apr. 22, 2015

(65) Prior Publication Data

US 2015/0305935 A1    Oct. 29, 2015

Related U.S. Application Data

(60) Provisional application No. 61/983,310, filed on Apr. 23, 2014.

(51) Int. Cl.
*A61F 9/007* (2006.01)
*A61B 17/32* (2006.01)
(Continued)

(52) U.S. Cl.
CPC .......... *A61F 9/00736* (2013.01); *A61B 17/32* (2013.01); *A61F 9/00763* (2013.01);
(Continued)

(58) Field of Classification Search
CPC .. A61F 9/00736; A61F 9/00763; A61B 17/32; A61B 2017/00154;
(Continued)

(56) References Cited

U.S. PATENT DOCUMENTS 3,559,970 A    2/1971   Hamabe et al.
3,882,872 A    5/1975   Douvas et al.
(Continued)

FOREIGN PATENT DOCUMENTS

WO    2008079526 A2    7/2008
WO    2011149621 A1    12/2011
(Continued)

OTHER PUBLICATIONS

Written Opinion for Application No. PCT/US2015/027012, dated Jun. 25, 2015, 8 pages.
(Continued)

*Primary Examiner* — Katrina Stransky
(74) *Attorney, Agent, or Firm* — Abbott Medical Optics Inc.

(57) ABSTRACT

A vitrectomy apparatus is provided, including a pressure source, a cut valve connected to the pressure source, the cut valve configured to be turned on and off to provide pressure to selectively extend and retract a vitrectomy cutting device, a plurality of sensors provided at a plurality of points between the pressure source and the vitrectomy handpiece, and a controller configured to employ a function correlating a desired cut rate with a pressure source duty cycle and employ a different function when one sensor of the plurality of sensors senses a pressure outside a predetermined pressure range.

19 Claims, 10 Drawing Sheets

(51) Int. Cl.
*A61B 17/00* (2006.01)
*A61B 90/00* (2016.01)

(52) U.S. Cl.
CPC .............. *A61B 2017/00154* (2013.01); *A61B 2017/00194* (2013.01); *A61B 2017/00411* (2013.01); *A61B 2017/00544* (2013.01); *A61B 2090/064* (2016.02); *A61B 2090/065* (2016.02)

(58) Field of Classification Search
CPC A61B 2017/00194; A61B 2017/00411; A61B 2017/00544; A61B 2090/064; A61B 2090/065
USPC ........................................................ 606/171
See application file for complete search history.

(56) References Cited

U.S. PATENT DOCUMENTS

| | | | |
|---|---|---|---|
| 4,314,560 | A | 2/1982 | Helfgott et al. |
| 4,768,506 | A | 9/1988 | Parker et al. |
| 5,279,547 | A | 1/1994 | Costin |
| 5,403,276 | A | 4/1995 | Schechter et al. |
| 5,417,246 | A | 5/1995 | Perkins et al. |
| 5,549,139 | A | 8/1996 | Perkins et al. |
| 5,788,667 | A | 8/1998 | Stoller |
| 5,857,485 | A | 1/1999 | Perkins et al. |
| 5,979,494 | A | 11/1999 | Perkins et al. |
| 6,010,496 | A | 1/2000 | Appelbaum et al. |
| 6,258,111 | B1 | 7/2001 | Ross et al. |
| 6,290,690 | B1 | 9/2001 | Huculak et al. |
| 6,506,176 | B1 | 1/2003 | Mittelstein et al. |
| 6,575,990 | B1 | 6/2003 | Wang et al. |
| 6,599,271 | B1 | 7/2003 | Easley |
| 6,599,277 | B2 | 7/2003 | Neubert |
| 6,689,089 | B1 | 2/2004 | Tiedtke et al. |
| 7,335,217 | B2 | 2/2008 | Wang et al. |
| 8,460,324 | B2 | 6/2013 | Gerg et al. |
| 8,818,564 | B2 | 8/2014 | Zhou et al. |
| 8,986,332 | B2 | 3/2015 | Gerg et al. |
| 2001/0029335 | A1 | 10/2001 | Juan et al. |
| 2002/0173814 | A1 | 11/2002 | Jung et al. |
| 2003/0195538 | A1 | 10/2003 | Wang et al. |
| 2005/0096682 | A1 | 5/2005 | Daffer |
| 2005/0113715 | A1 | 5/2005 | Schwindt et al. |
| 2007/0078506 | A1 | 4/2007 | McCormick et al. |
| 2007/0088376 | A1 | 4/2007 | Zacharias |
| 2008/0114372 | A1 | 5/2008 | Edwards et al. |
| 2008/0146988 | A1 | 6/2008 | Olivera et al. |
| 2008/0154292 | A1 | 6/2008 | Huculak et al. |
| 2008/0208207 | A1 | 8/2008 | Huculak et al. |
| 2008/0208233 | A1 | 8/2008 | Barnes et al. |
| 2009/0143734 | A1 | 6/2009 | Humayun et al. |
| 2009/0259242 | A1 | 10/2009 | Gerg et al. |
| 2010/0156646 | A1 | 6/2010 | Cull et al. |
| 2011/0054508 | A1 | 3/2011 | Zhou et al. |
| 2011/0077626 | A1 | 3/2011 | Baerveldt et al. |
| 2011/0144675 | A1 | 6/2011 | Gao et al. |
| 2011/0295293 | A1 | 12/2011 | Agahi |
| 2011/0295296 | A1 | 12/2011 | Charles |
| 2012/0053486 | A1 | 3/2012 | Huculak |
| 2012/0157879 | A1 | 6/2012 | Mark et al. |
| 2012/0157906 | A1 | 6/2012 | Underwood et al. |
| 2012/0158029 | A1 | 6/2012 | Underwood et al. |
| 2012/0158030 | A1 | 6/2012 | Underwood et al. |
| 2012/0165724 | A1 | 6/2012 | Auld et al. |
| 2012/0310146 | A1 | 12/2012 | Easley |
| 2013/0060210 | A1 | 3/2013 | Ross et al. |
| 2013/0144317 | A1 | 6/2013 | Valencia |
| 2013/0158578 | A1 | 6/2013 | Ghodke et al. |
| 2014/0114336 | A1 | 4/2014 | Schmitz et al. |
| 2014/0171991 | A1 | 6/2014 | Lee et al. |
| 2014/0171993 | A1 | 6/2014 | Lynn et al. |
| 2015/0148836 | A1* | 5/2015 | Heeren ............... A61F 9/00781 606/170 |

FOREIGN PATENT DOCUMENTS

| | | |
|---|---|---|
| WO | 2014099982 A1 | 6/2014 |
| WO | 2014099993 A1 | 6/2014 |
| WO | 2014105531 A1 | 7/2014 |

OTHER PUBLICATIONS

International Search Report and Written Opinion for Application No. PCT/US2013/075771, dated Apr. 2, 2014, 13 pages.
International Search Report and Written Opinion for Application No. PCT/US2013/075788, dated Apr. 3, 2014, 13 pages.
International Search Report and Written Opinion for Application No. PCT/US2013/075815, dated Apr. 24, 2014, 14 pages.
International Search Report for Application No. PCT/US2015/027012, dated Jun. 25, 2015, 5 pages.

* cited by examiner

VITRECTOMY SURGICAL APPARATUS EMPLOYING MULTISENSOR PRESSURE FEEDBACK

CROSS REFERENCE TO RELATED APPLICATION

This application claim priority to U.S. Provisional Application No. 61/983,310, filed on Apr. 23, 2014, entitled "Vitrectomy Surgical Apparatus Employing Multisensor Pressure Feedback," the entirety of which is incorporated by reference as if set forth herein.

BACKGROUND

Field of the Invention

The present invention relates generally to the field of surgical repair of retinal disorders, and more specifically to the efficient operation of pneumatic vitrectomy devices during ophthalmic surgical procedures.

Description of the Related Art

Vitrectomy surgery has been successfully employed in the treatment of particular ocular problems, such as retinal detachments resulting from tears or holes in the retina. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port.

Current vitreous cutting devices may employ a "guillotine" type action wherein a sharp-ended inner rigid cutting tube moves axially inside an outer sheathing tube. When the sharp-ended inner tube moves past the forward edge of a side port opening in the outer sheathing tube, the eye material (e.g. vitreous gel or fibers) is cleaved into sections small enough to be removed through the hollow center of the inner cutting tube.

Vitreous cutters are available in either electric or pneumatic form. Today's electric cutters may operate within a range of speeds typically between 750-2500 cuts-per-minute (CPM) where pneumatic cutters may operate over a range of speeds between 100-2500 CPM. The surgeon may make adjustments to control the pneumatic vitrectomy surgical instrument cutting speed, i.e. controlling the cutting device using a surgical handpiece, in order to perform different activities during the corrective procedure. Corrective procedures may include correction of macular degeneration, retinal detachment, macular pucker, and addressing eye injuries.

The cutting device within a pneumatic handpiece requires precise control of applied pressure to overcome the internal spring return mechanism to assure the quality of each cutting stroke. Such systems have typically employed a fluid (typically air) reservoir or accumulator to collect fluid and from which fluid is drawn to effectuate the cut valve using pneumatic pressure. The frequency of opening and closing the pneumatic valve, i.e. the time interval between each opening cycle of the valve, is varied to achieve the desired cutting speed. In order to power the cut valve and cutter at a consistent pressure for an extended period of time, a relatively large fluid reservoir or accumulator is needed. A large fluid reservoir is undesirable in today's operating environment where smaller components are favored. Further, in this type of environment, inconsistent pressure can be provided to the cut valve in even the best of circumstances, and in the case of minor leaks, inconsistent pressure is practically a given. Even minor pressure inconsistencies can be highly undesirable.

Additionally, current systems employ calibration settings to account for changes in the operating room environment. Calibration settings can accommodate for relatively fixed environmental factors, such as altitude, but rapidly changing environmental factors such as temperature or electro-mechanical pump variations in virtually all situations cannot be adequately addressed using calibration techniques.

Based on the foregoing, it would be advantageous to provide a system that enables pneumatic cutting functionality at relatively consistent cutting pressures that reduce or eliminate the need for a relatively large fluid reservoir or accumulator. Such a system would have an ability to provide consistent cutting pressures under different conditions typically encountered in a vitrectomy surgical room environment.

SUMMARY

Thus according to one aspect of the present invention, there is provided a vitrectomy apparatus comprising a pressure source, a cut valve connected to the pressure source, the cut valve configured to be turned on and off to provide pressure to selectively extend and retract a vitrectomy cutting device, a plurality of sensors provided at a plurality of points between the pressure source and a vitrectomy handpiece, and a controller configured to selectively provide commands to change pressure source duty cycle according to a plurality of linear functions when one sensor of the plurality of sensors measures a pressure outside a predetermined pressure range.

According to another aspect of the present design, there is provided a method for controlling a vitrectomy system, comprising sensing pressure provided from a pressure source through a cut valve and to a vitrectomy handpiece using a plurality of sensors positioned between the pressure source and the vitrectomy handpiece, and controlling operation of the cut valve based on pressure measured by altering a function when measured pressure from one of the plurality of sensors is outside a predetermined pressure range.

According to another aspect of the present design, there is provided a vitrectomy apparatus comprising a vitrectomy handpiece comprising a vitrectomy cutting device, a sensing arrangement comprising a plurality of sensors configured to sense pressure, tubing connecting the vitrectomy handpiece to the sensing arrangement, a cut valve connected to the sensing arrangement, a pressure source configured to provide pressure to the cut valve, and a controller configured to receive data from the sensing arrangement and selectively provide commands to change pressure source duty cycle according to a plurality of linear functions according to data received from the sensing arrangement.

Other features and advantages of the present invention should be apparent from the following description of exemplary embodiments, which illustrate, by way of example, aspects of the invention.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for high-speed pneumatic vitrectomy control and operation that employs pressure feedback at various points in the pneumatic line, thereby reducing or eliminating the need for a fluid reservoir or accumulator space in a vitrectomy machine. Such a design enables more accurate and efficient cutting of the vitreous material.

The present design is directed to accurate, reliable, and efficient control of the cutting speed of the blade in a pneumatic vitrectomy handpiece used in a medical instrument system. The present design will be discussed herein with a particular emphasis on a medical or hospital environment where a surgeon or health care practitioner performs. For example, an embodiment of the present design is a phacoemulsification surgical system that comprises an integrated high-speed control module for the vitrectomy handpiece. The surgeon may adjust or set the cutting speed via a graphical user interface (GUI) module or a foot pedal switch to control the high-speed pneumatic vitrectomy handpiece.

Figure 1A:
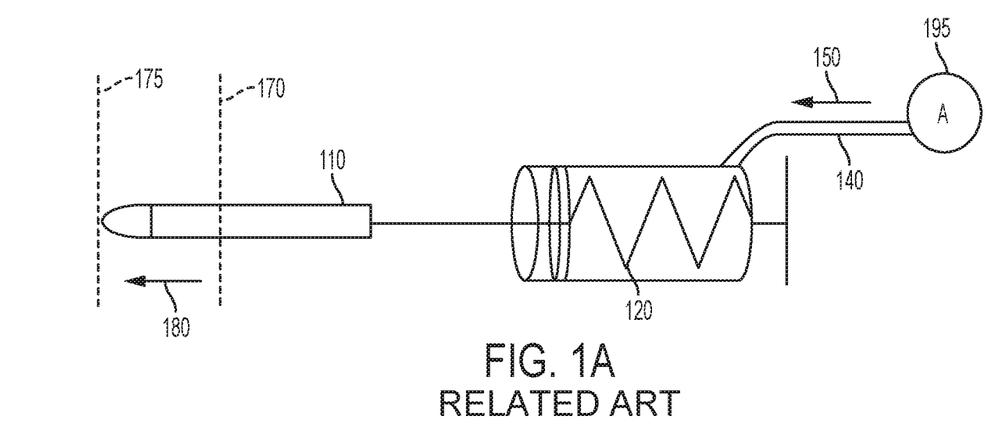
FIG. 1A illustrates a common vitrectomy system's pneumatic cutting mechanism, located within a surgical handpiece, with the pneumatic cutting mechanism extended in a "cut," "closed port," or "forward" position.
Figure 1B:
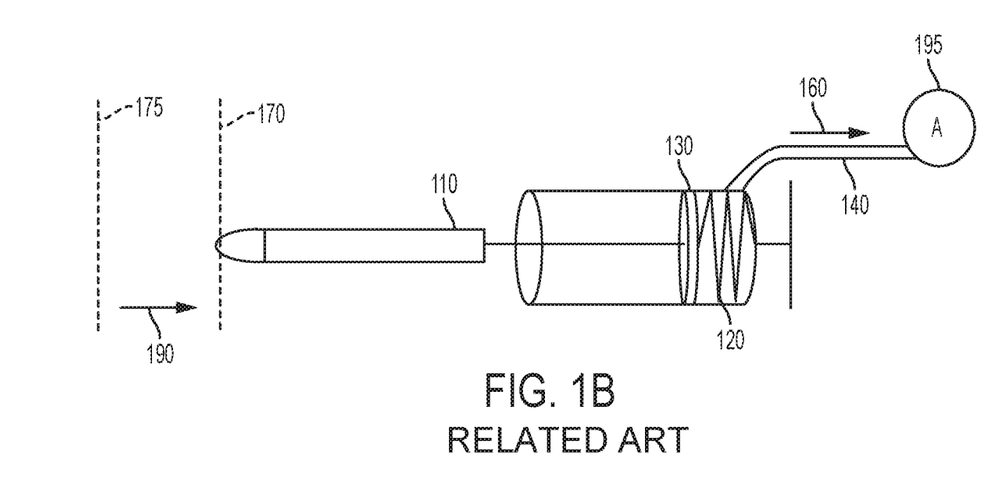
FIG. 1B shows a common vitrectomy system's pneumatic cutting mechanism, located within a surgical handpiece, with the pneumatic cutting mechanism spring retracted in an "initial," "open port," or "backward" position.

FIGS. 1A and 1B are high-level conceptual block diagrams illustrating a common vitrectomy system's pneumatic cutting mechanism located within a surgical handpiece provided for purposes of explaining the present invention. FIG. 1A shows the pneumatic cutting mechanism in the "cut," "closed port," or "forward" position, while FIG. 1B shows the pneumatic cutting mechanism in the "initial," "open port," or "backward" position. Referring to FIGS. 1A and 1B, construction of pneumatic cutter devices typically involve a blade 110 positioned to work or operate against a spring 120 by inflating and deflating a bladder 130 configured to move blade 110 by 'pushing' blade 110 forward to a forward position 175 when bladder 130 is inflated and 'pulling' blade 110 backward using the energy stored in spring 120 to its resting position or initial position 170 when bladder 130 is deflated. The desired cutting speed may be realized by filling and emptying bladder 130 in a cyclical manner through an air passage 140 arranged for receiving a pressurized airburst in the direction indicated at point 150. The received pressurized air burst is then evacuated or vented in direction 160.

Current designs are generally configured to cyclically inflate and deflate bladder 130 to move blade 110 in a forward direction 180 and backward direction 190, thus producing the desired cutting action. A combination input pressurized air supply and output air venting valve mechanism 195, or valve, is represented in FIGS. 1A and 1B.

In order to control the speed of blade 110, currently available pneumatic designs typically use a control signal to open and close valve 195. Valve 195 may be configured to provide a pressurized airburst when the valve is open, filling bladder 130 and venting the air within bladder 130 when the valve is closed to empty the bladder. Increasing the frequency of the control signal cycling rate, which produces a shorter pressurized air burst time, generally results in an increased cutting speed, or an increased number of cuts-per-minute as observed at the knife or blade. A subsequent decrease in control signal cycling rate generally produces a slower or decreased cutting speed.

Figure 2A:
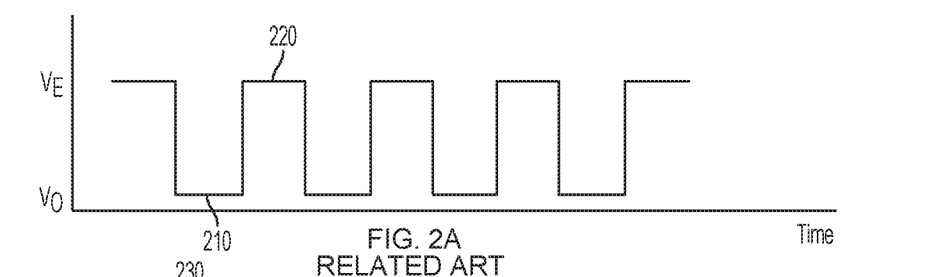
FIG. 2A is a graph illustrating a typical cyclical control signal used for opening and closing a valve by setting the valve to either an energizing or a de-energizing state.
Figure 2B:
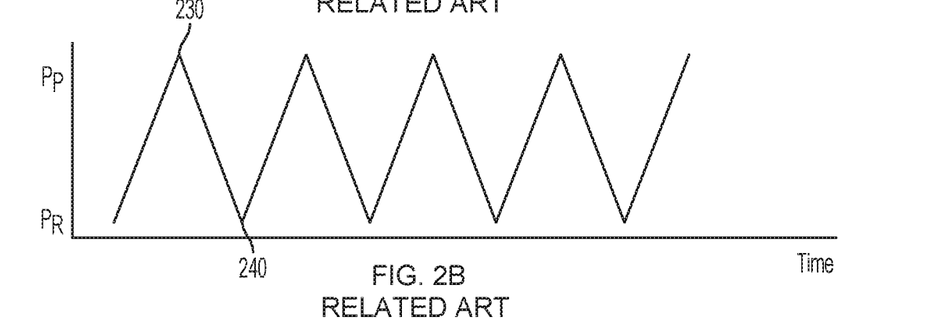
FIG. 2B is a graph illustrating an output pressure waveform resulting from the control signal illustrated in FIG. 2A.

Previous designs have employed control signals to drive the cutter. One example control signal to instruct the opening and closing of valve 195 associated with air passage 140 is shown in FIG. 2A. The control signal illustrated in FIG. 2A may cycle between valve-off ($V_O$) at point 210 and valve-on ($V_E$) at point 220, or provide a valve-energized instruction at a predetermined cycling rate, thereby effectuating the desired cutting speed. FIG. 2B illustrates an example pressure waveform resulting from the application of the control signal shown in FIG. 2A. The waveform is shown to have a constant rise in pressure up to a peak pressure ($P_P$) at 230 when the valve is energized. A subsequent drop in pressure to a residual pressure ($P_R$) at point 240 occurs when the valve is de-energized. The cycling in pressure, for controlling the blade forward and backward reciprocating movements, as illustrated by the waveform shown in FIG. 2B, may produce a specific cutting speed for blade 110 in terms of cuts-per-minute.

Pneumatic cutter designs have been configured with a speed control device to select and vary the rate the blade mechanism moves forward and backward to effectuate cutting. In these designs, changing the speed of the blade may involve varying the time or duration of the control signal provided to the valve. By increasing the open period and closed period of valve 195, the resultant blade speed is reduced. Likewise, decreasing the amount of time valve 195 is open and closed causes the blade speed to increase.

Figure 2C:
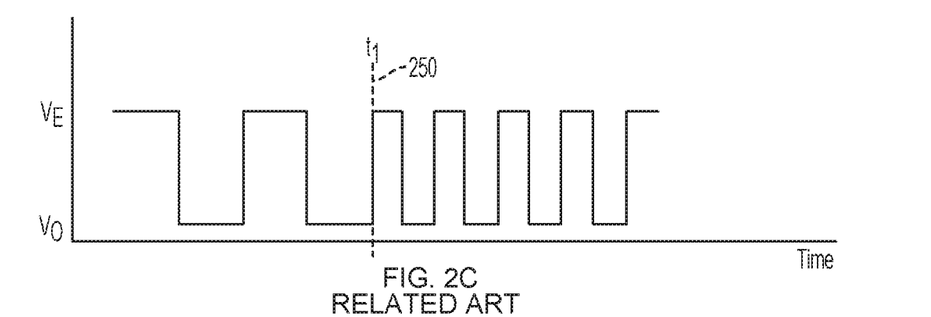
FIG. 2C is a graph illustrating the cyclical control signal applied to a valve where at a specific instance in time the frequency is increased.
Figure 2D:
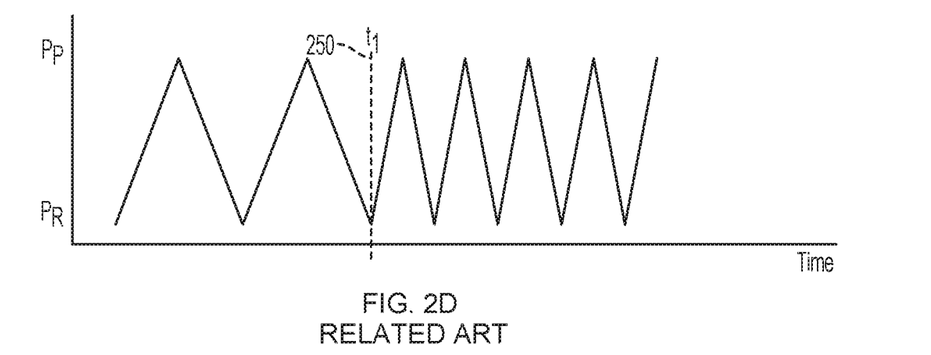
FIG. 2D is a graph illustrating a pressure waveform resulting from the change in the cyclical control signal frequency as illustrated in FIG. 2C.

An example of a control signal for controlling the filling and emptying of air in bladder 130 with an increase in cycle time is illustrated in FIG. 2C. Before time $t_1$ at 250, the control signal cyclic frequency is set at a lower rate than after time $t_1$ to illustrate the surgeon selecting an increase in cutting speed at time $t_1$ during a surgical procedure. FIG. 2D illustrates an example pressure waveform resulting from the application of the control signal shown in FIG. 2C. This pressure waveform reflects the control signal change that occurred at time $t_1$ at 250, and may drive blade 110 at a faster rate.

The pneumatic vitrectomy handpiece is used in connection with a phaco-vitrectomy module and may be part of a phacoemulsification machine. Such a handpiece may include a "guillotine" type cutter pneumatically driven to either an open or closed position. Opening and closing occurs via air pressure provided via a flexible line or delivery line between the cutter and a pneumatic driver. The pneumatic driver may include a pressure source, such as a pump, configured to fill a small reservoir or accumulator with compressed air at its maximum pressure capacity. As employed herein, the terms "accumulator" and "reservoir" are used interchangeably and are intended to mean the same fluid (typically air) buffering or holding device. The output of this reservoir is connected to a pressure regulator that may regulate the air pressure down to the level required by the cutter, as shown by peak $P_P$ and residual $P_R$ pressure in FIG. 2B. A smaller reservoir may be supplied or fed by the regulator output, forming the source for the delivery valve.

The cutter in the present vitrectomy embodiment is pneumatic, while the cut valve actuation is electrical. The pulsing discussed is an electrical signal transmitted from the control module. When the electrical pulse drops to a non-energized state, a vent is opened resulting in a drop in pressure that functions to enable the force of a spring to overcome the resultant pressure, and the cutter returns to an initial state.

The electronic controller may be connected to the delivery valve and may provide instructions to produce a pulse width (in time) of pressurized air when the valve is open. The controller may be arranged to provide fixed pulses of pressurized air within the flexible line in a manner that drives the cutter. The electronic controller may use a fixed pulse timing control signal to instruct the delivery valve to open and close. The fixed timing, or fixed duration, control signal instructs the delivery valve to open and close in a constant cyclical manner. When the flexible line is at zero or near zero pressure, for example refer to residual pressure $P_R$ shown in FIG. 2B, the cutter is biased toward the initial or resting position. The cutter closes when the air pressure in the cutter delivery line exceeds a predetermined value between $P_R$ and $P_P$. When the delivery valve is off, the air in the cutter tubing is exhausted through the valve exhaust port. The cutter then returns to the initial position when the pressure in the delivery line decreases close to atmospheric pressure, i.e. $P_R$.

The foregoing description generally discloses the components and control functionality of prior vitrectomy devices. Such control functionality can be characterized as "open-loop," or without any type of feedback. Cutting speeds, etc. are simply set by a surgeon or user and effectuated, and changes in conditions or parameters in the environment are unaccounted for.

Figure 3:
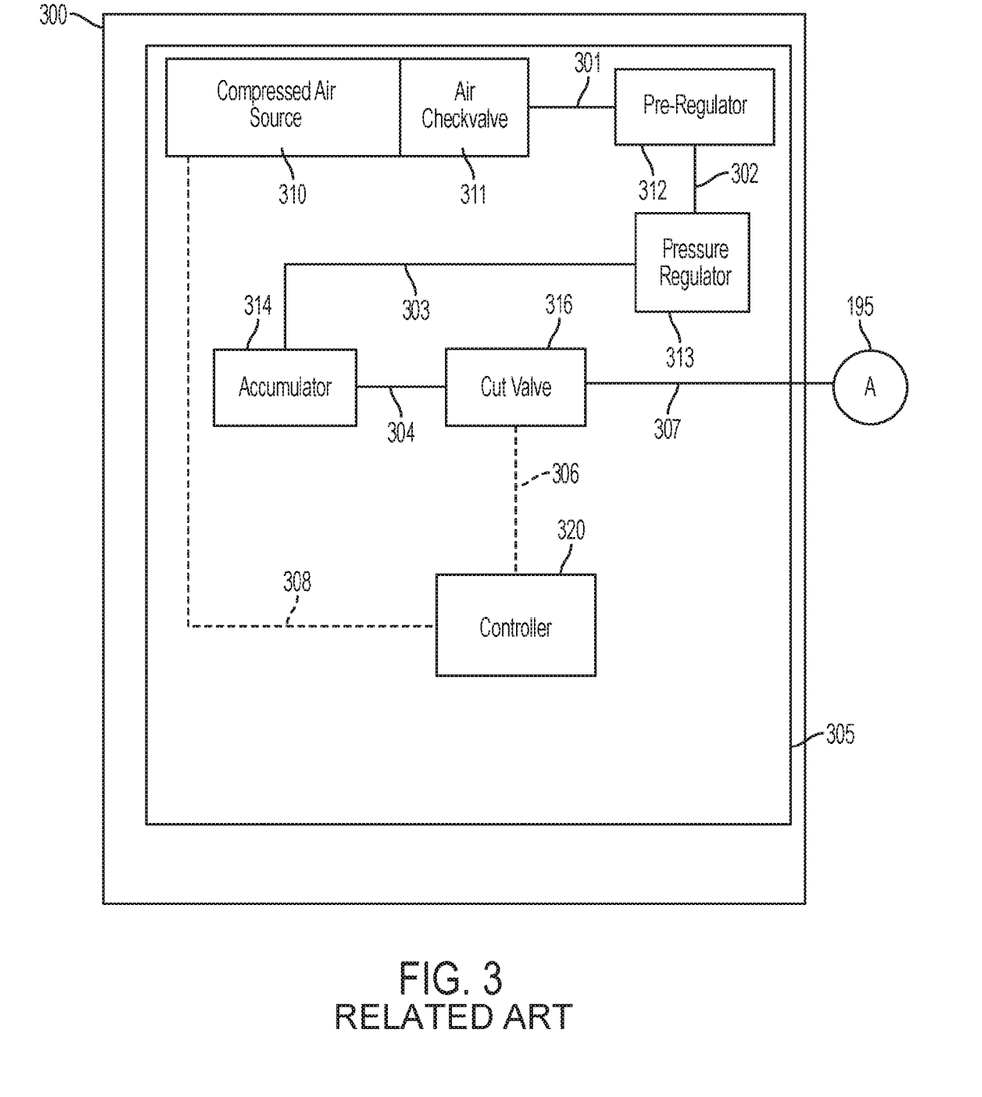
FIG. 3 is a block diagram illustrating components and devices for a prior art pneumatic vitreous cutting module integrated within a phacoemulsification machine in accordance with the present design.

FIG. 3 is a block diagram illustrating components and devices for a previous version of a pneumatic vitreous cutting module 305 integrated within a phacoemulsification machine 300 in accordance with the present design. Although depicted as an integral unit, module 305 functionality may be realized by using multiple devices to perform the functionality disclosed. From FIG. 3, a compressed air source 310 and associated air check valve 311 may supply air pressure for pneumatic vitreous cutting module 305. The compressed air source 310 typically comprises a pump (not shown) configured to both provide a pneumatic, typically a gas such as air, supply pressure to the cut valve and a vent mechanism to relieve pressure to atmospheric conditions. Compressed air source 310 thus provides a source of vacuum or pressure. Compressed air is provided by the pump via delivery line 301 illustrated between air check valve 311 and pre-regulator 312. Check valve 311 is typically arranged with two ports and may allow air pressure to flow through in one direction, from compressed air source 310 to pre-regulator 312. The pump may pump pressurized air into a high pressure chamber, not shown, which in turn provides high pressure air to pre-regulator 312 via delivery line 301. The high-pressure chamber or compressed air source 310 may provide a stable source of air at a higher pressure than the working pressure of the cutter.

As used herein, the term "pressure source" or the "compressed air source" means any device or arrangement that is configured to provide a source of pressure or vacuum, including but not limited to a pump or Venturi device, compressed air supply, compressed air inlet supply, or any device provided within a vitrectomy machine or originating from an external source that provides pressure or vacuum, such as a pressure source provided through a wall of a building, e.g. via a wall mounted nozzle or device, an external pressure source such as an external pump, or otherwise. The terms are therefore intended to be interpreted broadly.

Pre-regulator 312 may provide a workable steady air pressure stream from which compressed air source 310 may supply air pressure for pressure regulator 313 via delivery line 302. Pressure regulator 313 may be preset to a desired pressure and may be configured to provide air to accumulator 314 at a low,-steady, and safe operating pressure. Pressure regulator 313 may connect directly to compressed air source 310, typically a pump, but alternately a high pressure chamber, by a delivery line and input high pressure and regulate the air pressure to a lower value consistent with the operating pressure of the cutter handpiece.

Accumulator 314 may operate as a working pressure chamber, and may receive pressurized air at specific pressure and volume from pressure regulator 313 via delivery line 303. Accumulator 314 may provide a specific amount of air pressure at a predetermined volume to cut valve 316 via delivery line 304 such that no excess pressure is forced into the delivery line 307.

Controller 320, which may provide a graphical user interface, computes a cut rate based on physician input (programmed and/or the footpedal position) or the pre-programmed maximum cut rate and/or the footpedal position and electronically provides a desired or computed cut rate to cut valve 316 via communications control line 306. The controller 320 may take different forms, including comprising a PCBA (printed circuit board assembly), or may be part of a PCBA, ASIC, or other hardware design. A storage unit (not shown) may be provided to store certain values used by the controller 320 during the vitrectomy procedure, including settings desired by the surgeon and other relevant data. Cut valve 316 may open and close in response to the control signal provided from controller 320. Controller 320 electronically controls the valves operating the regulated pressure and/or vacuum air sent to the cutter. The handpiece blade motion may move in a forward and backward reciprocating motion in response to the pressure waveform provided via delivery line 307.

During operation, controller 320 may operate cut valve 316 to deliver a pulse of regulated air pressure to delivery line 307 and the cutter (not shown). While the surgeon or practitioner may select variations in the pulse repetition frequency, once the selection is made, the system seeks to attain the desired cutting rate.

Cut valve 316 is electronically controlled by controller 320 to transmit pressure, and cut valve 316 opens and closes at a precise time to allow air at a specific pressure and volume to fill the delivery line 307 and operate the cutter. Cut valve 316 may connect to atmospheric pressure for purposes of venting air received from delivery line 307. Controller 320 may provide an electronic indication to cut valve 316 that originates with a user selected switch, such as a switch on the handpiece, graphical user interface, or a foot switch. Line 308 represents the electrical connection between controller 320 and compressed air source 310.

The present design employs pressure feedback at multiple points in the line between the compressed air source 310 and valve 195, and feedback of the pressures at the various points is employed in a specific manner to control cut pressure.

Figure 4:
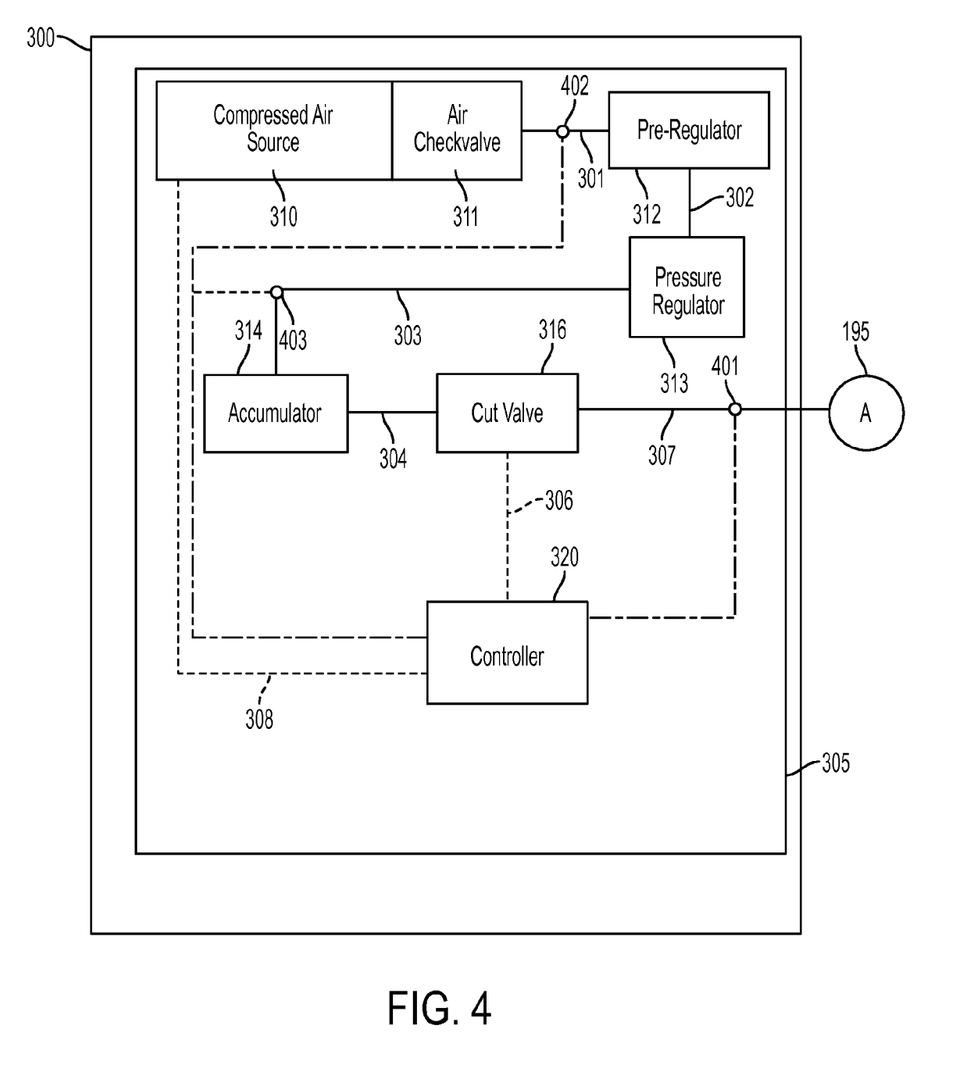
FIG. 4 is an embodiment of a vitrectomy device according to the present design.

FIG. 4 illustrates an embodiment of a vitrectomy device according to the present design. A number of components in FIG. 4 are identical to those of FIG. 3. As shown in FIG. 4, sensors 401, 402, and 403 are provided, where sensor 401 is provided at the cut valve 195, sensor 402 is provided between the compressed air source 310 and the pre-regulator 312, and sensor 403 is provided between pressure regulator 313 and accumulator 314. Each of sensors 401, 402, and 403 provide signals to controller 320, typically in the form of current pressure sensed.

Thus, the present design includes a vitrectomy apparatus having a compressed air source such as a pump, a cut valve connected to the pump, the cut valve configured to be turned on and off to provide pressure to selectively extend and retract a vitrectomy cutting device, a plurality of sensors configured to sense pressure provided along the line between the pump and the vitrectomy cutting device, and a controller configured to control the duty cycle of the pump based on a linear function selected based on pressure sensed by the plurality of sensors. The pressure source comprises a pump having a pump core and a pressure regulator configured to control pressure supplied from the pump core.

Figure 5:
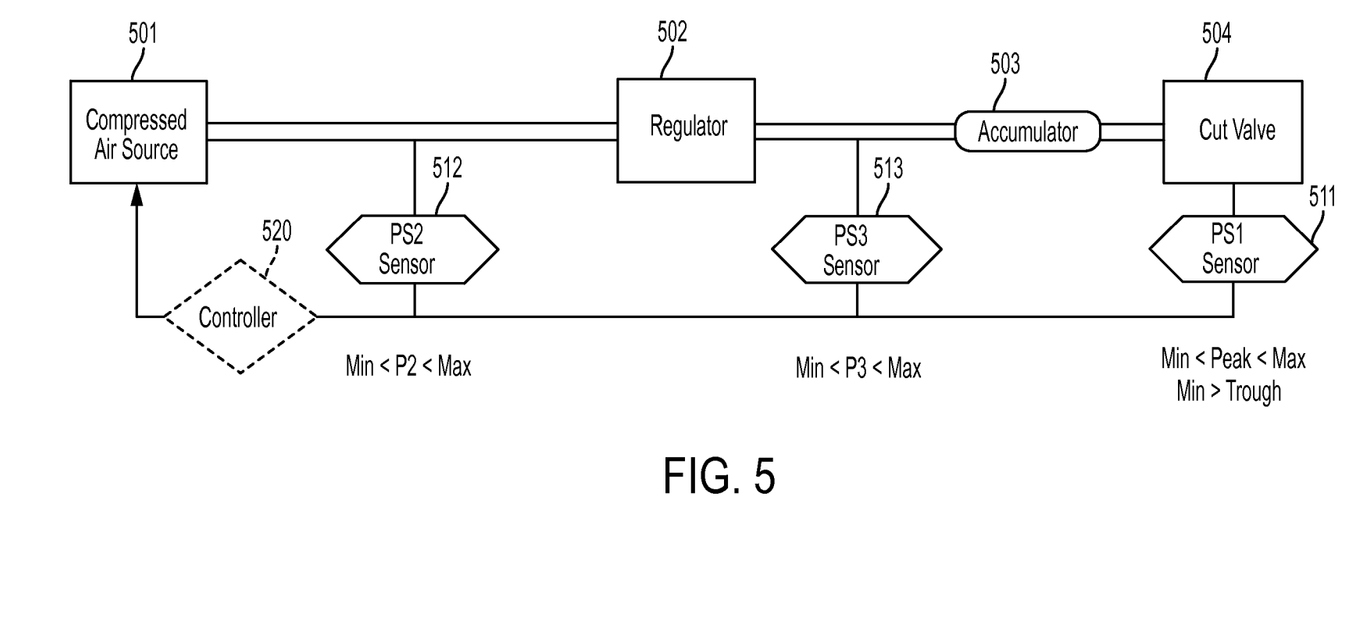
FIG. 5 is an alternate embodiment of the present design.

FIG. 5 presents an alternate embodiment of the present design. FIG. 5 shows compressed air source 501, regulator 502, accumulator 503, and cut valve 504 in a single line and connected as shown. Pressure sensor 511 measures or senses (collectively, "measures") pressure at cut valve 504, while pressure sensor 513 measures pressure at a point between regulator 502 and accumulator 503. Pressure sensor 512 measures the pressure between compressed air source 501 and regulator 502. As shown, each of sensors 511, 512, and 513 feeds information to controller 520, which then controls compressed air source 501 based on information received from the sensors.

In general, pressure sensor 511 measures pressure and in conjunction with the controller 520 determines whether the peak value during a period of time is between a first set minimum and maximum allowable value. These components also determine whether the measured value of pressure sensor 513 is between a third set of minimum and maximum values, while pressure sensor 512 and controller 520 determine whether the pressure at the pressure sensor 512 is between a second set of minimum and maximum values.

Sensors in FIG. 5 are illustrated as separate from the line, i.e. not specifically in line, while sensors in FIG. 4 are shown in line. Sensors can be positioned either in line or separate, but in either situation the sensor functions to determine the air pressure in the positions shown. In one embodiment, each sensor comprises a passage configured to monitor pneumatic pressure at a point between the compressed air source and the vitrectomy cutting device, and the controller comprises circuitry configured to provide signals to control the pump duty cycle based on a linear function selected based on pressure sensed or measured by the plurality of sensors.

Further, FIG. 4 illustrates the sensor 402 provided between the compressed air source 310 and the pre-regulator 312, however in an embodiment the sensor may be placed elsewhere, such as between pre-regulator 312 and pressure regulator 313.

Figure 6:
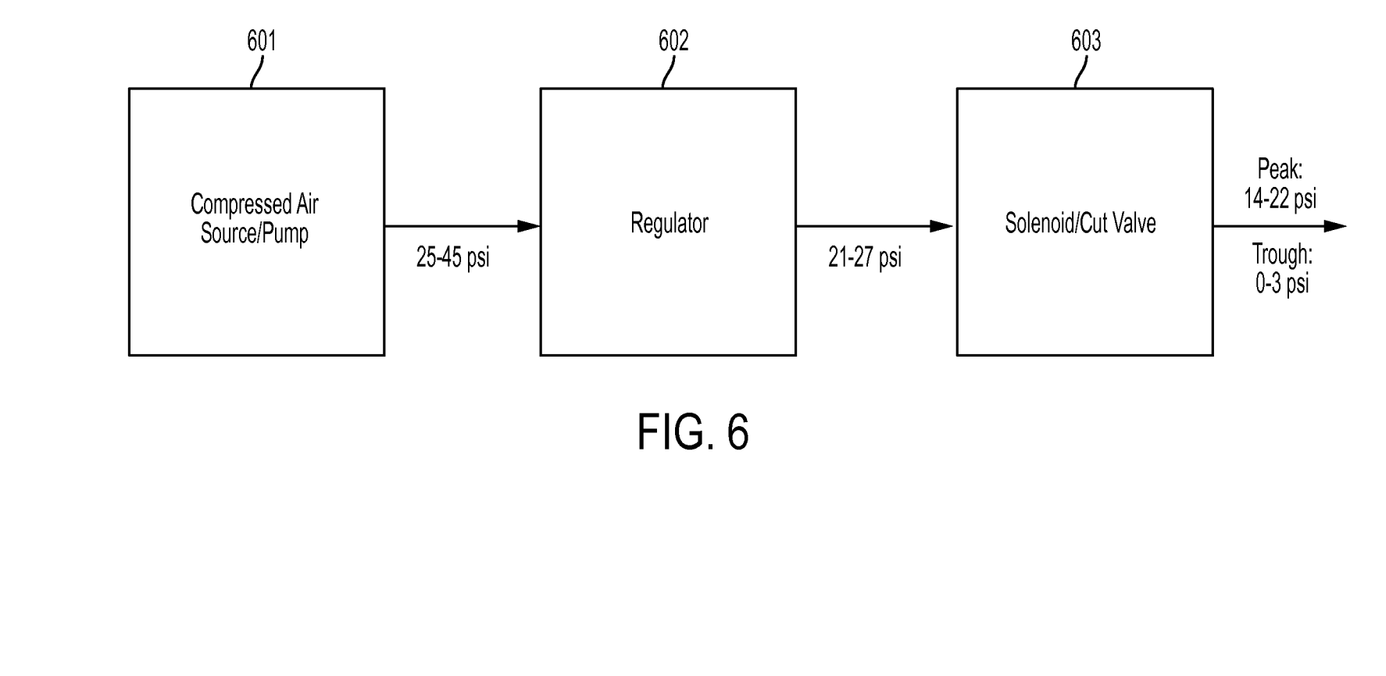
FIG. 6 is a simplified view of the present design reflecting certain maximum and minimum predetermined pressure values employed in a particular arrangement.

FIG. 6 is a simplified view of the present design reflecting certain maximum and minimum predetermined pressure values employed in a particular arrangement. Numbers presented are generally representative but may change depending on circumstances and equipment employed. From FIG. 6, compressed air source 601 provides pressure to regulator 602 in an expected range of between about 25 and 45 psi. Pressure between regulator 602 and cut valve 603 is expected to be between about 21 and 27 psi. Pressure at cut valve 603 is expected to have a trough, or lowest, value of between zero and three psi, with a peak between 14 and 22 psi, irrespective of cut speed. Again, these are representative values and actual values may differ, but the values may differ between the three sensors as far as acceptable pressure ranges. While three sensors are shown in this embodiment, it is to be understood that any number of sensors may be employed that is typically greater than one.

In operation, the controller such as controller 320 in FIG. 3, employs a function, typically a linear function, to drive the speed of the compressed air source 310 or pump 601 to deliver a relatively steady source of pressure to the cut valve. Controller 320 monitors the sensors, typically at a very rapid rate such as in the tens of milliseconds. If the pressure at any sensor of the multiple sensors varies outside the expected range, the system changes the function (e.g. linear function) employed. In an embodiment, if the pressure at any sensor of the multiple sensors varies outside the expected range, the system changes the function employed by increasing or decreasing a linear function constant depending upon whether greater or lower pressure is required.

Employing this type of design, including regulating compressed air source pressure, enables the design to employ an accumulator or reservoir that is measurably smaller than accumulators previously employed. Further, in certain instances, the need for an accumulator may be eliminated entirely.

Figure 7:
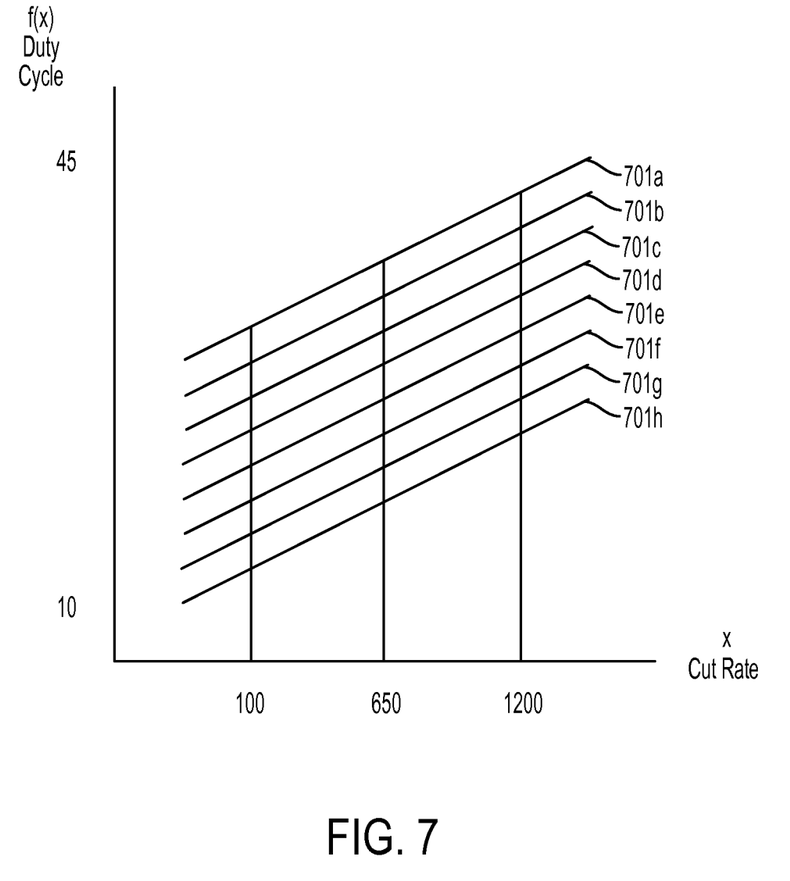
FIG. 7 illustrates representative duty cycle graphs or curves according to one aspect of the present design.

FIG. 7 illustrates representative duty cycle graphs or curves according to one aspect of the present design. The y axis of FIG. 7 represents the motor duty cycle, i.e. the speed of the motor driving the compressed air source, while the x axis represents the cut rate. Again, these curves are representative of expected curves and values in a typical setting, but the values may differ for different settings, components, and/or circumstances, and any number of curves may be employed. In FIG. 7, eight curves are shown as an example, and each of the curves 701a-h may be employed depending on circumstances. In one instance, a default curve may be employed and a different curve employed as time progresses, e.g. a curve above or below the default curve may be selected depending on pressures encountered. One example curve may be provided as:

$$F(x) = (1/100)x + (\text{MinDuty} - 1) \quad (1)$$

From Equation (1), x represents the cut rate desired, or provided by the surgeon or operator. As an example, the requested cut rate may be 1200 CPM. MinDuty is the minimum acceptable duty cycle, in percent, and a number as low as 10 is not unusual in certain operations. For an example minimum duty cycle of 10 percent, Equation (1) would provide $(1/100)*1200+(10-1)$, or a value of 21 for the motor duty cycle.

The value $1/100$, or the slope of the function or curve, is generally calculated as the maximum duty cycle minus the minimum duty cycle desired for performance over the range divided by the maximum cut rate minus the minimum cut rate expected for the device. Thus while numbers may vary depending on circumstances including cut range and pump duty cycles, a number such as $1/100$ may be appropriate in certain instances.

Cut rate in certain pneumatic applications may be, for example, between 100 and 1200 CPM. In this particular application, duty cycle varies based on the pump motor employed, but in some circumstances, a minimum duty cycle of 10 percent and a maximum duty cycle of 45 percent is not unexpected. The present design switches between functions, in this embodiment between linear functions, when one of the three sensors senses a pressure above a highest value or below a lowest value, the controller 320 changes the function to adapt to changes in environment. Such a design may serve to maintain or improve cut pressure even when a leak is present in the system or more specifically in the line.

In general, if the pressure at any of the sensed points is less than the corresponding threshold, the linear function constant is incremented resulting in the duty cycle being incremented if not already at an upper limit. If pressure at any of the sensors is greater than the corresponding threshold, the linear function constant is decremented resulting in the duty cycle being decremented if not already at a lower limit. The result is a new function, i.e. a new linear function when pressure is outside an expected range, when the linear function is not already at an upper or lower limit.

Figure 8:
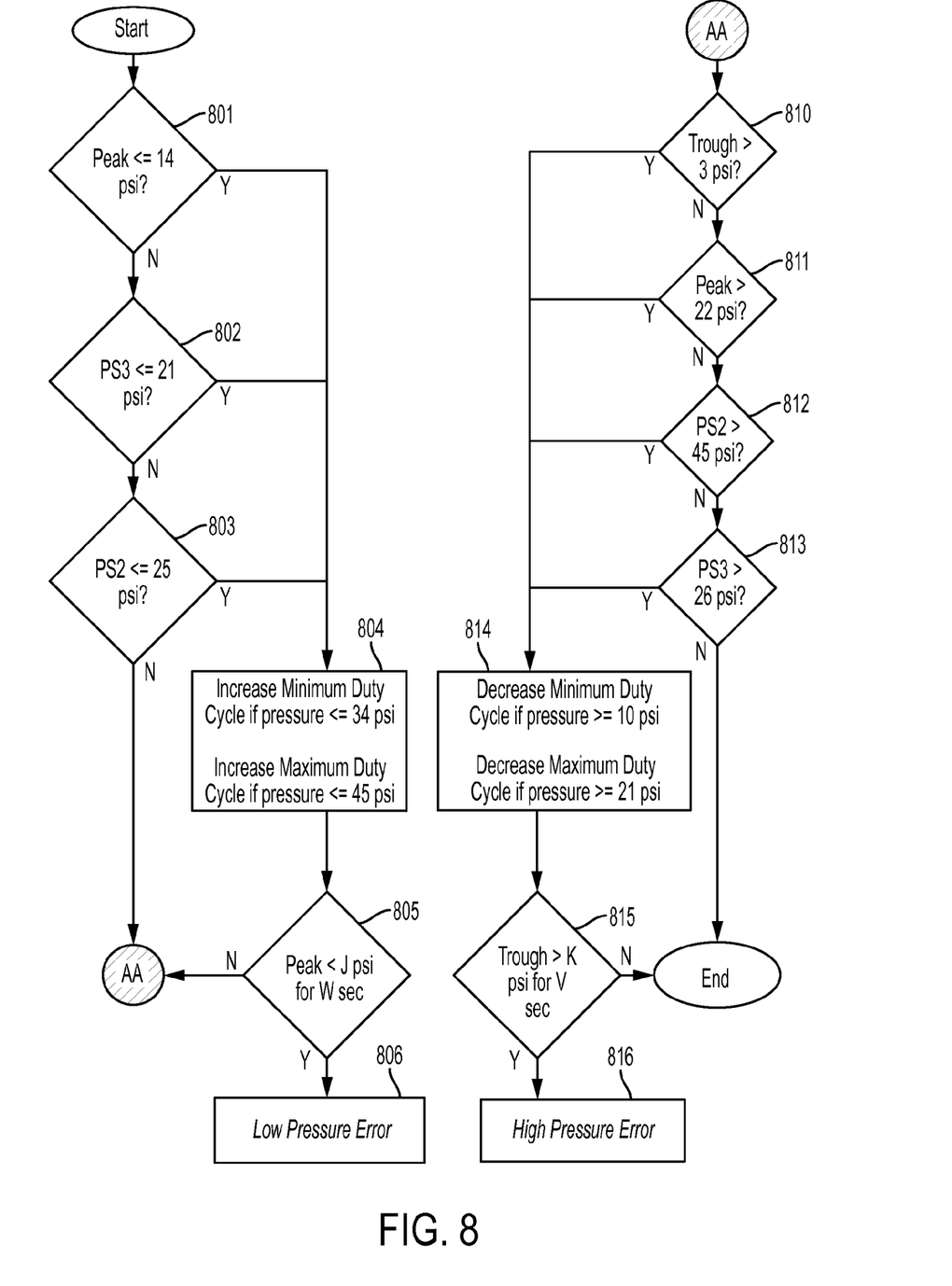
FIG. 8 is a general flowchart depicting operation of the controller based on sensed pressures.

FIG. 8 is a general flowchart depicting operation of the controller based on sensed pressures. From FIG. 8, operation begins at point 801 and runs through low pressure evaluation and adjustment. Note that the particular functions depicted in FIG. 8 may occur in any order or in different groupings than shown. For example, FIG. 8 shows making low pressure assessments and adjustments before high pressure assessments and adjustments, but these may reversed, and/or ordering of the sensors evaluated and pressures addressed may differ from the depiction shown. At point 801, the system assesses the cutter sensor, e.g. first sensor 511 in FIG. 5, and determines if the peak value is less than or equal to a predetermined value, shown as 14 psi in this embodiment. If the peak value sensed is less than or equal to this predetermined value, operation progresses to point 804, but if not, operation progresses to point 802. At point 802, the system determines whether pressure sensed at, for example, third sensor 513 in FIG. 5, and the pressure is evaluated as being less than or equal to a predetermined level, in this embodiment 21 psi. Again, if the pressure is less than or equal to, operation transitions to point 804, but if not, operation passes to point 803, wherein pressure sensed at second pressure sensor 512 in FIG. 5, is evaluated. If the pressure at second pressure sensor 512 is less than or equal to a predetermined amount, such as 25 psi, operation transitions to point 804. If not, this indicates that every sensor has sensed a pressure above the requisite minimums, and operation transitions in this embodiment to high pressure sensing and adjustment.

Point 804 indicates that the minimum duty cycle is increased to less than or equal to a desired value, such as 34 psi, and the maximum duty cycle is also increased to less than or equal to a desired value, such as 45 psi. Point 805 evaluates whether the peak value has been less than an acceptable value for a predetermined amount of time. If not, there is no current issue, and processing progresses to high pressure assessment and adjustment. If so, a low pressure error exists, which may be any number of problems including but not limited to a severe break in the line(s). In this failure situation, failure processing may occur, including providing warnings and/or shutting down operation in a safe and approved manner.

At point 810, the system assesses the cutter sensor, e.g. first sensor 511 in FIG. 5, and determines if the trough value is greater than a predetermined value, shown as 3 psi in this embodiment. If the trough or lowest value sensed is greater than this predetermined value, operation progresses to point 814, but if not, operation progresses to point 811. At point 811, the system determines whether the peak value is greater than a predetermined value, in this embodiment greater than 22 psi. If so, operation progresses to point 814, and if not, operation progresses to point 812. At point 812, the pressure sensed at, for example, second sensor 512 in FIG. 5, is evaluated as being greater than a predetermined level, in this embodiment 45 psi. Again, if the pressure is greater, operation transitions to point 814, but if not, operation passes to point 813, wherein pressure sensed at third pressure sensor 513 in FIG. 5, is evaluated. If the pressure at third pressure sensor 513 is greater than a predetermined amount, such as 27 psi, operation transitions to point 814. If not, this indicates that every sensor has sensed a pressure below the established maximums, and operation is complete for this functionality.

Point 814 indicates that the minimum duty cycle is decreased to a value of greater than or equal to a desired value, such as 10 psi, and the maximum duty cycle is also decreased to greater than or equal to a desired value, such as 21 psi. Point 815 evaluates whether the trough value has been greater than a predetermined value for a certain amount of time. If not, there is no current issue, and processing ends. If so, a high pressure error exists. In this failure situation, failure processing may occur, including providing warnings and/or shutting down operation, again in a safe and approved manner.

Thus the present design takes pressure readings from multiple positions along the line and alters functions when the pressures sensed are above or below predetermined values. In this manner, a more robust maintenance of cutting pressure, either at a high cutting speed or a low cutting speed, is maintained without the need for a large accumulator. Sensor measurements may be evaluated at an appropriate rate, such as in the tens of milliseconds, e.g. from between 10 to 100 milliseconds. Advantages may be gained by evaluating at different points along the path before others; for example, if concern is great regarding pressure at the cut valve, the cut valve sensor may be evaluated first. If concern is greatest regarding compressed air source pressure, the sensor closest to the compressed air source may be evaluated first. Evaluations may be done in parallel or in any order desired, and operation is not in any way limited to the depiction provided in FIG. 8.

Vitrectomy Performance

Figure 9:
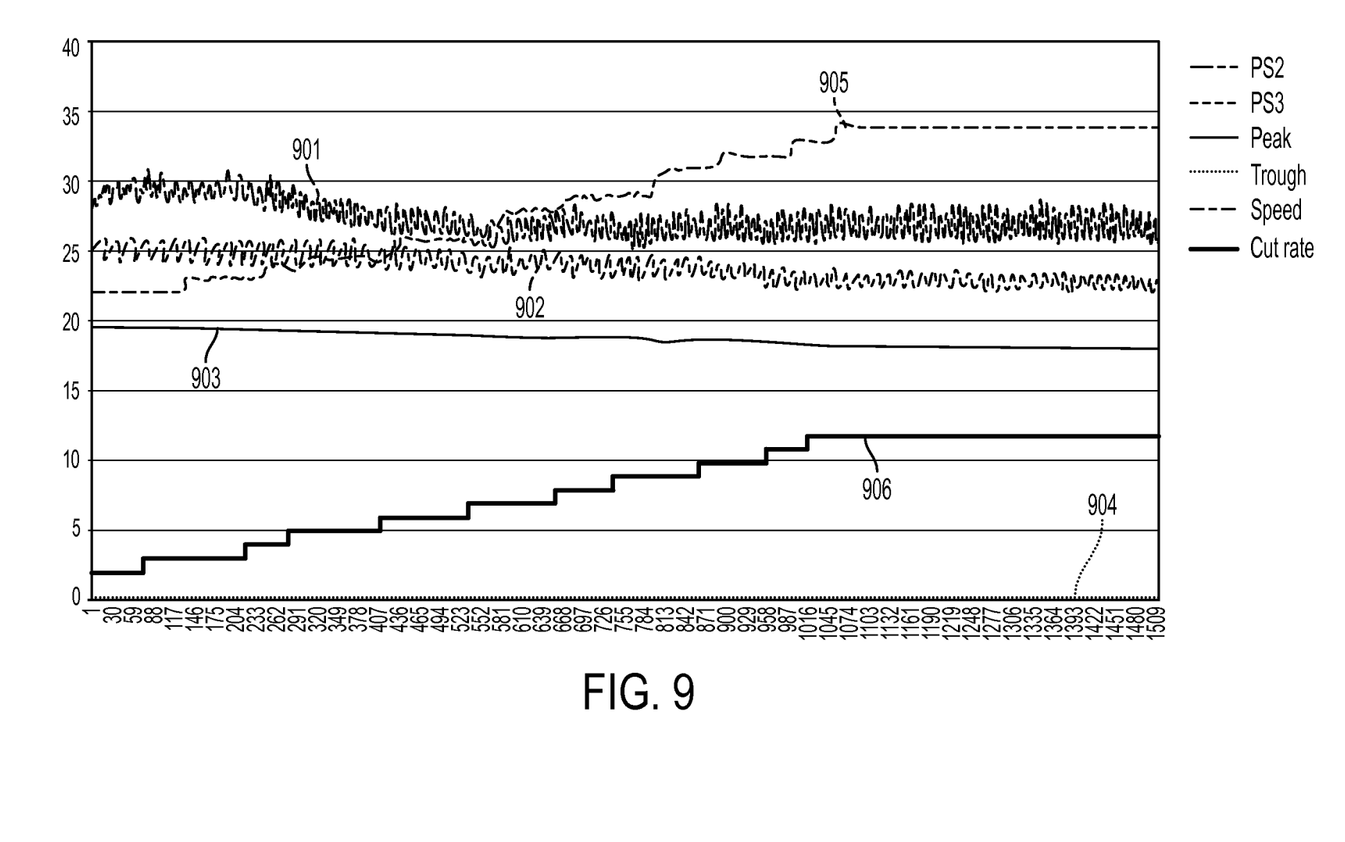
FIG. 9 illustrates performance of continuous vitrectomy at various cut rates according to one embodiment of the present design.

FIG. 9 illustrates closed loop control of the compressed air source or pump according to an embodiment of the present design. FIG. 9 illustrates the vitreous cutter running continuously and stepped from a low value to a high value, in one embodiment from 100 CPM to 1200 CPM. Pump motor duty cycle, labeled as Speed in FIG. 9, shows that compensation follows the same basic stepping pattern as the requested cut rate, labeled as Cut-Rate in FIG. 9. While the duty cycle follows the stepping pattern of the requested cut rate, the peak pressure, labeled Peak, as well as the pump pressure (PS2) and the regulator pressure (PS3) are consistent in amplitude.

FIG. 9 specifically represents one embodiment, with PS2 (line 901) being pump pressure in psi, ranging from 21 to 45 psi, PS3 (line 902) being regulator pressure in psi, from 21 to 25, Peak (line 903) being a peak pressure level, from 14 to 22 psi, Trough (line 904) being a trough or low pressure between 0 and 3 psi. Speed (line 905) represents the speed of the compressed air source motor, while Cut Rate (line 906) represents the cut rate. The x axis of FIG. 9 represents time, while the y axis is motor duty cycle, or pressure in psi, or cut rate divided by 100 depending on the variable. These values and conditions represent a single embodiment, and different readings, parameters, values, speeds, and so forth may be encountered while still within the scope of the present invention.

Figure 10:
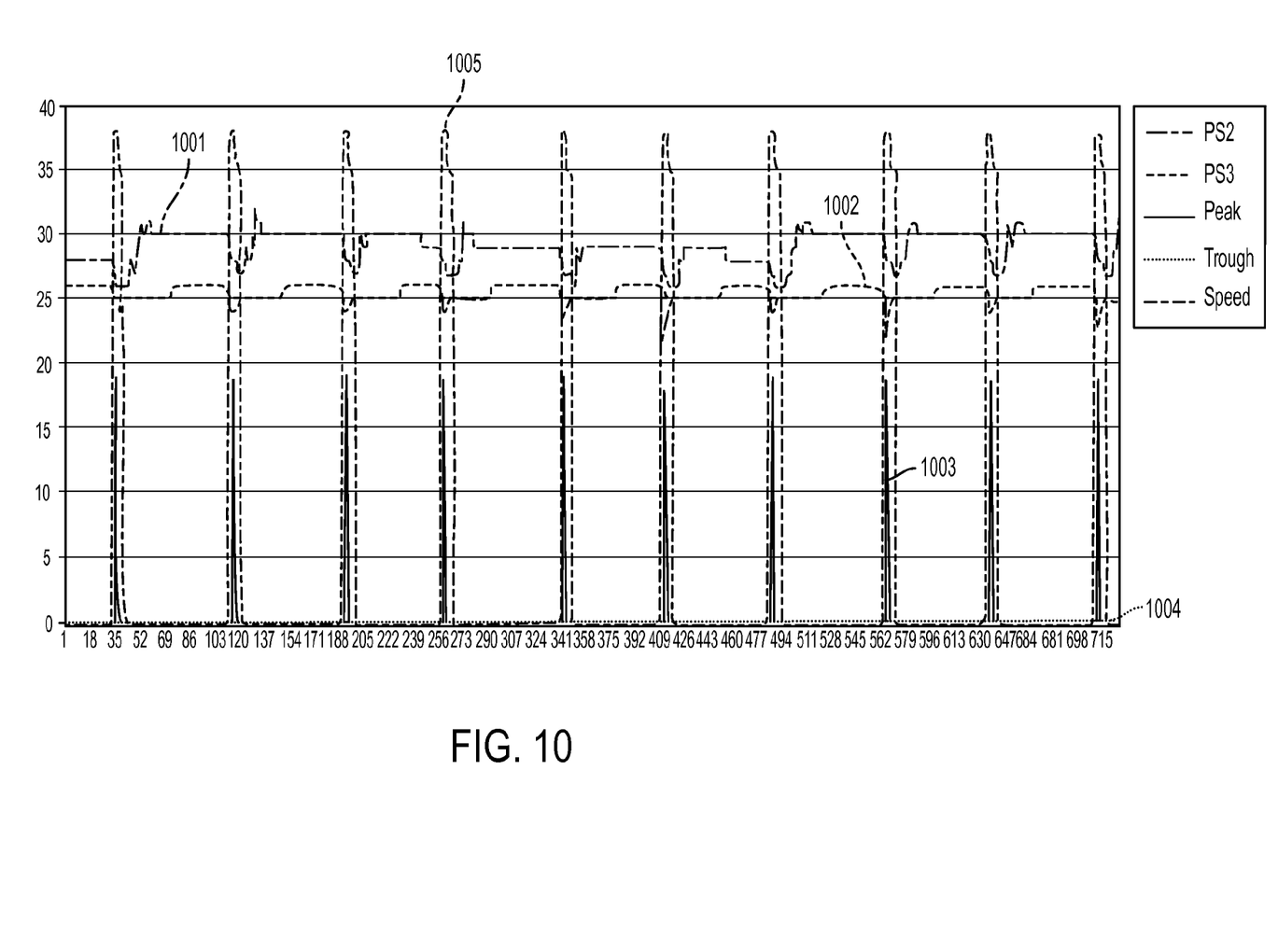
FIG. 10 is performance of repeated single cut vitrectomy according to one embodiment of the present design.

FIG. 10 shows an example vitreous cutter making repeated single cuts. In this embodiment, the data shows the effect of the compensating closed-loop software control of the duty cycles of the pneumatic pump, i.e. the effect of the linear functions. The corresponding data for the pump motor duty cycle (Speed, line 1005) shows the compensation for each single cut remains consistent as does peak pressure, labeled as Peak (line 1003), pressure at the pump, labeled PS2 (line 1001), and pressure at the regulator, labeled PS3 (line 1002). As with FIG. 9, FIG. 10 represents a particular embodiment, with PS2 (line 1001) being pump pressure in psi, ranging from 21 to 45 psi, PS3 (line 1002) being regulator pressure in psi, from 21 to 25, Peak (line 1003) being a peak pressure level, from 14 to 22 psi, Trough (line 1004) being a trough or low pressure between 0 and 4 psi. Speed (line 1005) represents the duty cycle of the compressed motor source. The x axis of FIG. 10 represents time, while the y axis is motor duty cycle or pressure in psi depending on the variable. Again, these values and conditions represent a single embodiment, and different readings, parameters, values, speeds, and so forth may be encountered while still within the scope of the present invention.

Though discussed herein with respect to a surgical device and more specifically a vitrectomy cutter, the present approach may be used to control any pneumatic device wherein pressures vary or need to be varied over time. Pneumatic devices driven by varying pressures may include devices used for cutting, hammering, or lifting.

Thus the present design includes a vitrectomy apparatus, comprising a pressure source, a cut valve connected to the pressure source, the cut valve configured to be turned on and off to provide pressure to selectively extend and retract a vitrectomy cutting device, a plurality of sensors provided at a plurality of points between the pressure source and the cut valve, and a controller configured to employ a function correlating a desired cut rate with a pressure source duty cycle and employ a different function when one sensor of the plurality of sensors senses a pressure outside a predetermined pressure range.

Alternately, the present design is a method for performing a vitrectomy procedure, comprising sensing pressure provided from a pressure source through a cut valve and to a vitrectomy handpiece using a plurality of sensors positioned between the pressure source and the vitrectomy cutting device, and controlling operation of the cut valve based on pressure sensed by altering a function when sensed pressure from one of the plurality of sensors is outside a predetermined pressure range.

Another embodiment of the present design is a vitrectomy apparatus, comprising a vitrectomy handpiece comprising a vitrectomy cutting device, a sensing arrangement comprising a plurality of sensors configured to sense pressure, tubing connecting the vitrectomy handpiece to the sensing arrangement, a cut valve connected to the sensing arrangement, a pressure source configured to provide pressure to the cut valve, and a controller configured to receive data from the sensor arrangement and selectively provide commands to change pressure source duty cycle according to a plurality of linear functions according to data received from the sensor arrangement.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, DOM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A vitrectomy apparatus, comprising:
   a pressure source;
   a cut valve connected to the pressure source, the cut valve configured to be turned on and off to provide pressure to selectively extend and retract a vitrectomy cutting device;
   a plurality of sensors provided at a plurality of points between the pressure source and a vitrectomy handpiece; and
   a controller configured to selectively provide commands to change pressure source duty cycle according to a function selected from a plurality of functions that each calculate a duty cycle for a given cut rate, wherein each of the plurality of functions returns a different duty cycle than the other functions of the plurality of functions, for at least one given cut rate, the function being selected from the plurality of functions when one sensor of the plurality of sensors measures a pressure outside a predetermined pressure range.

2. The vitrectomy apparatus of claim 1, wherein the function is a linear function.

3. The vitrectomy apparatus of claim 1, wherein the pressure source comprises a pump comprising a pump core and a pressure regulator configured to control pressure supplied from the pump core.

4. The vitrectomy apparatus of claim 1, wherein each sensor comprises a passage configured to monitor pneumatic pressure at a point between the cut valve and the vitrectomy cutting device.

5. The vitrectomy apparatus of claim 4, wherein the controller is configured to monitor pressure and control duty cycle based on readings received from three sensors positioned between the pressure source and the vitrectomy handpiece.

6. The vitrectomy apparatus of claim 1, wherein the controller is configured to:
   change the function thereby changing the pressure source duty cycle when one sensed pressure received from the plurality of sensors is outside a predetermined pressure range.

7. A method for controlling a vitrectomy system, comprising:
   sensing pressure provided from a pressure source through a cut valve and to a vitrectomy handpiece using a plurality of sensors positioned between the pressure source and the vitrectomy handpiece; and
   controlling pressure delivered to the cut valve based on pressure measured by selecting a function from a plurality of functions that each calculate a duty cycle for a given cut rate, wherein each of the plurality of functions returns a different duty cycle than the other functions of the plurality of functions, for at least one given cut rate, the function being selected from the plurality of functions when measured pressure from one of the plurality of sensors is outside a predetermined pressure range.

8. The method of claim 7, wherein controlling operation of the cut valve comprises controlling a duty cycle of the pressure source.

9. The method of claim 7, wherein pressure is sensed by a first pressure sensor positioned proximate the pressure source and a second pressure sensor positioned proximate the cut valve.

10. The method of claim 9, wherein pressure is further sensed by a third pressure sensor positioned between the first pressure sensor and the second pressure sensor.

11. The method of claim 7, wherein the controlling comprises monitoring pressure and controlling duty cycle based on readings received from three sensors positioned between the pressure source and the vitrectomy handpiece.

12. The method of claim 7, wherein the function comprises a first linear function and controlling operation comprises employing the first linear function during operation and changing to employing a second linear function when sensed pressure is outside the predetermined range.

13. The method of claim 7, wherein the function is a linear function and wherein controlling operation further comprises:
   changing a constant associated with the linear function thereby changing the pressure source duty cycle when one sensed pressure received from the plurality of sensors is outside a first predetermined pressure range.

14. The method of claim 7, wherein the pressure source comprises a pump comprising a pump core and a pressure regulator configured to control pressure supplied from the pump core.

15. A vitrectomy apparatus, comprising:
   a vitrectomy handpiece comprising a vitrectomy cutting device;
   a sensing arrangement comprising a plurality of sensors configured to sense pressure;
   tubing connecting the vitrectomy handpiece to the sensing arrangement;
   a cut valve connected to the sensing arrangement;
   a pressure source configured to provide pressure to the cut valve; and
   a controller configured to receive data from the sensing arrangement and selectively provide commands to change pressure source duty cycle according to a function selected from a plurality of functions that each calculate a duty cycle for a given cut rate, wherein each of the plurality of functions returns a different duty cycle than the other functions of the plurality of functions, for at least one given cut rate, the function being selected from the plurality of functions according to data received from the sensing arrangement.

16. The vitrectomy apparatus of claim 15, wherein the pressure source comprises a pump comprising a pump core and a pressure regulator configured to control pressure supplied from the pump core.

17. The vitrectomy apparatus of claim 15, wherein each sensor comprises a passage configured to monitor pneumatic pressure at a point between the cut valve and the vitrectomy cutting device, and the controller comprises circuitry configured to provide signals to control a pump motor duty cycle based on pressure measured by the plurality of sensors.

18. The vitrectomy apparatus of claim 17, wherein the controller is configured to monitor pressure and control duty cycle to maintain pressure based on readings received from three sensors positioned between the pressure source and the vitrectomy handpiece.

19. The vitrectomy apparatus of claim 15, wherein the controller is configured to:
   change the function thereby changing the pressure source duty cycle when one measured pressure received from the plurality of sensors is outside a predetermined pressure range.

* * * * *